US008632703B2

(12) United States Patent
Robin

(10) Patent No.: US 8,632,703 B2
(45) Date of Patent: Jan. 21, 2014

(54) AZEOTROPIC AND AZEOTROPE-LIKE COMPOSITIONS OF E-1,1,1,4,4,5,5,5-OCTAFLUORO-2-PENTENE

(75) Inventor: Mark L. Robin, Middletown, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 866 days.

(21) Appl. No.: 12/676,665

(22) PCT Filed: Sep. 5, 2008

(86) PCT No.: PCT/US2008/075345
§ 371 (c)(1),
(2), (4) Date: Mar. 17, 2010

(87) PCT Pub. No.: WO2009/032983
PCT Pub. Date: Mar. 12, 2009

(65) Prior Publication Data
US 2010/0243943 A1 Sep. 30, 2010

Related U.S. Application Data

(60) Provisional application No. 60/970,393, filed on Sep. 6, 2007, provisional application No. 60/993,254, filed on Sep. 11, 2007, provisional application No. 60/993,240, filed on Sep. 11, 2007, provisional application No. 61/012,846, filed on Dec. 11, 2007, provisional application No. 61/012,848, filed on Dec. 11, 2007, provisional application No. 61/021,132, filed on Jan. 15, 2008, provisional application No. 61/021,139, filed on Jan. 15, 2008, provisional application No. 61/021,145, filed on Jan. 15, 2008.

(51) Int. Cl.
A62D 1/00 (2006.01)
C09K 5/00 (2006.01)
C09K 5/10 (2006.01)
H01B 3/24 (2006.01)
C11D 17/00 (2006.01)

(52) U.S. Cl.
USPC ............... 252/570; 252/2; 252/69; 252/78.1; 252/364; 510/415

(58) Field of Classification Search
USPC .................... 252/364, 78.1, 570, 69; 510/415
See application file for complete search history.

(56) References Cited

U.S. PATENT DOCUMENTS

| | | | |
|---|---|---|---|
| 3,085,918 A | 4/1963 | Sherliker et al. |
| 3,723,318 A | 3/1973 | Butler |
| 3,884,828 A | 5/1975 | Butler |
| 4,085,073 A | 4/1978 | Suh et al. |
| 4,394,491 A | 7/1983 | Hoffman |
| 4,613,708 A | 9/1986 | Riess et al. |
| 4,704,410 A | 11/1987 | Booth et al. |
| 4,704,411 A | 11/1987 | Gansow et al. |
| 5,037,572 A | 8/1991 | Merchant |
| 5,164,419 A | 11/1992 | Bartlett et al. |
| 5,204,159 A | 4/1993 | Tan |
| 5,332,761 A | 7/1994 | Paquet et al. |
| 5,463,150 A | 10/1995 | Lui et al. |
| 5,578,137 A | 11/1996 | Shealy |
| 5,900,185 A | 5/1999 | Tapscott |
| 5,908,822 A | 6/1999 | Dishart |
| 5,977,271 A | 11/1999 | McKay et al. |
| 6,071,580 A | 6/2000 | Bland et al. |
| 6,590,005 B2 | 7/2003 | Singh et al. |
| 6,610,250 B1 | 8/2003 | Tuma |
| 6,703,431 B2 | 3/2004 | Dietzen et al. |
| 6,787,580 B2 | 9/2004 | Chonde et al. |
| 2004/0119047 A1 | 6/2004 | Singh et al. |
| 2004/0256594 A1 | 12/2004 | Singh et al. |

(Continued)

FOREIGN PATENT DOCUMENTS

DE 2534315 2/1976
EM 350316 B1 2/1997

(Continued)

OTHER PUBLICATIONS

M. Taverna et. al., "Soluble or Insoluble Alternative Blowing Agents? Processing Technologies for Both Alternatives, Presented by Equipment Manufacturer", Published in Polyurethanes World Congress 1991 From the Proceedings of the SPI/SOPA Sep. 24-26, 1991, Acropolis, Nice, France.
Santini G. et. al., "The Reaction of Perfluoroalkylcopper Compounds With 1-Bromo-Perfluoroalkyethylenes", Tetrahedron, vol. 29, 1973, pp. 2411-2414, XP002427778, Table 3; Compound 2A, 2B.
Devallezbernard et. al., "Solubility of Respiratory Gases in the 1, 2-Bis(F-Alkyl) Ethenes", Journal De Chimie Physique, Societe De Chimie Physique, Paris, France, vol. 85, No. 10, 1988, pp. 947-952, XP008077143.
Gao et al., "Dip-Coating of Ultra Think Liquid Lubricant and Its Control for Thin-Film Magnetic Hard Disks", IEEE Transactions on Magnetics, vol. 31, No. 6, 1995, pp. 2982-2984.
Le Blanc M et. al., "A Strategy for the Synthesis of Pure, Inert Perfluoroalkylated Derivatives Designed for Flood Substitution", Oxygen Carrying C9olloidal Blood Substitues, Iinternational Symposium Perfluorochem Blood Substitutes, 1982, pp. 43-49, XP008077176.

(Continued)

Primary Examiner — Peter F Godenschwager

(57) ABSTRACT

Azeotropic or azeotrope-like compositions are disclosed. The azeotropic or azeotrope-like compositions are mixtures of E-1,1,1,4,4,5,5,5-Octafluoro-2-pentene with methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane or Z-1,1,1,4,4,4-hexafluoro-2-butene. Also disclosed is a process of preparing a thermoplastic or thermoset foam by using such azeotropic or azeotrope-like compositions as blowing agents. Also disclosed is a process of producing refrigeration by using such azeotropic or azeotrope-like compositions. Also disclosed is a process of using such azeotropic or azeotrope-like compositions as solvents. Also disclosed is a process of producing an aerosol product by using such azeotropic or azeotrope-like compositions as propellants. Also disclosed is a process of using such azeotropic or azeotrope-like compositions as heat transfer media. Also disclosed is a process of extinguishing or suppressing a fire by using such azeotropic or azeotrope-like compositions. Also disclosed is a process of using such azeotropic or azeotrope-like compositions as dielectrics. Also disclosed is a process for the separation of a chemical compound from a mixture of two or more chemical compounds using such azeotropic or azeotrope-like compositions.

3 Claims, 9 Drawing Sheets

(56) References Cited

U.S. PATENT DOCUMENTS

| | | |
|---|---|---|
| 2005/0233934 A1 | 10/2005 | Singh et al. |
| 2007/0077488 A1 | 4/2007 | Chen et al. |
| 2007/0096051 A1 | 5/2007 | Nappa et al. |
| 2007/0098646 A1 | 5/2007 | Nappa et al. |
| 2007/0100009 A1 | 5/2007 | Creazzo et al. |
| 2007/0100010 A1 | 5/2007 | Creazzo et al. |
| 2007/0100011 A1 | 5/2007 | Creazzo et al. |
| 2007/0102021 A1 | 5/2007 | Nappa et al. |
| 2007/0105738 A1 | 5/2007 | Nappa et al. |
| 2007/0108403 A1 | 5/2007 | Sievert et al. |
| 2007/0203045 A1* | 8/2007 | Schweitzer et al. .......... 510/411 |
| 2007/0203046 A1 | 8/2007 | Minor et al. |
| 2008/0269532 A1 | 10/2008 | Swearingen |

FOREIGN PATENT DOCUMENTS

| | | |
|---|---|---|
| EP | 0558763 A1 | 8/1993 |
| EP | 0398147 B1 | 9/1994 |
| EP | 0731162 A1 | 11/1996 |
| GB | 950876 | 2/1964 |
| JP | 05179043 | 7/1993 |
| WO | 94/23008 A1 | 10/1994 |
| WO | 2004/037913 A2 | 5/2004 |
| WO | 2005/099718 A1 | 10/2005 |
| WO | 2006/101882 A2 | 9/2006 |
| WO | 2008/057513 A1 | 5/2008 |
| WO | 2008/134061 A2 | 11/2008 |
| WO | 2008/154612 A1 | 12/2008 |
| WO | 2009/014965 A1 | 1/2009 |
| WO | 2009/014966 A1 | 1/2009 |
| WO | 2009/032983 A1 | 3/2009 |
| WO | 2009/073487 A1 | 6/2009 |
| WO | 2009/085857 A2 | 7/2009 |

OTHER PUBLICATIONS

F. Jeanneaux et al., "Additional Thermique Des IODO-1-Perfluoroalcanes Sur Les Perfluoroalkylethylenes", Journal of Fluorine Chemistry, 4 (1974), pp. 261-270.

World Meteorological Organization Global Ozone Research and Monitoring Project, Scientific Assessment of Ozone Depletion: 2002, "Source Gases", Report No. 47, Published Mar. 2003, pp. 1.28-1.31.

Skochdopole, R. E. et. al., "Polystyrene Foams", Encyclopedia of Polymer Science, vol. 16 (1989), pp. 193-206.

Pedler A. E. et. al., "The Synthesis and Dehydroflurination of Some Polyfluoroalkanes", J. Fluorine Chem., vol. 1 No. 3, 1972, pp. 337-345, XP002427764.

M. F. Doherty and M.F. Malone, Conceptual Design of Distillation Systems, McGraw-Hill (New York), 2001, 185-186, 351-359).

"Phase Equilibrium in Process Design", Wiley-Interscience Publisher, 1970, written by Harold R. Null, on pp. 124 to 126.

"The Properties of Gases and Liquids," 4th edition, published by McGraw Hill, written by Reid, Prausnitz and Poling, on pp. 241 to 387.

"Phase Equilibria in Chemical Engineering," published by Butterworth Publishers, 1985, written by Stanley M. Walas, pp. 165 to 244.

H. Boden et. al., Chapter 4, Polyurethane Handbook, Edited by G. Oertel, Hanser Publishers, NY 1985.

H. Grunbauer et. al., "Fine Celled CFC-Free Rigid Roam—New Machinery With Low Boiling Blowing Agents", Published in Polyurethanes 92 From the Proceedings of the SPI 34th Annual Technical/Marketing Conference, Oct. 21-24, 1992, New Orleans, Louisiana.

* cited by examiner

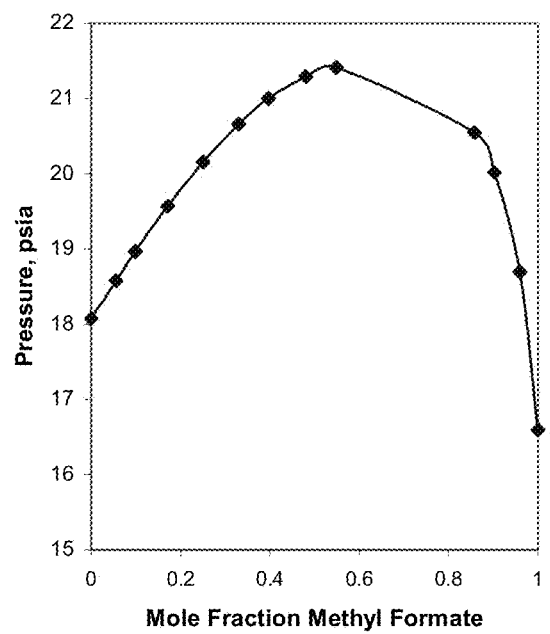

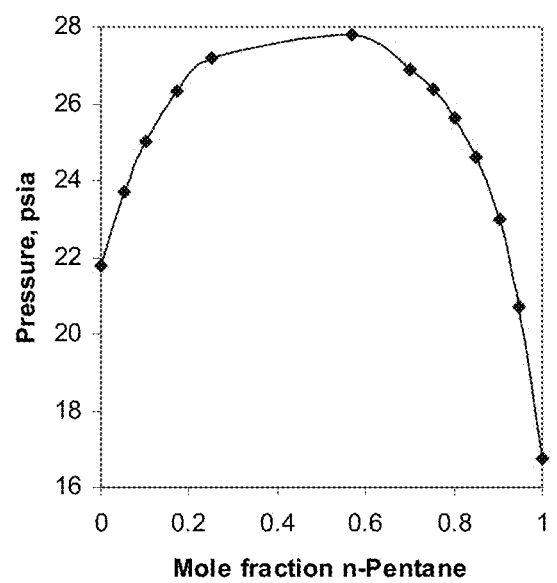

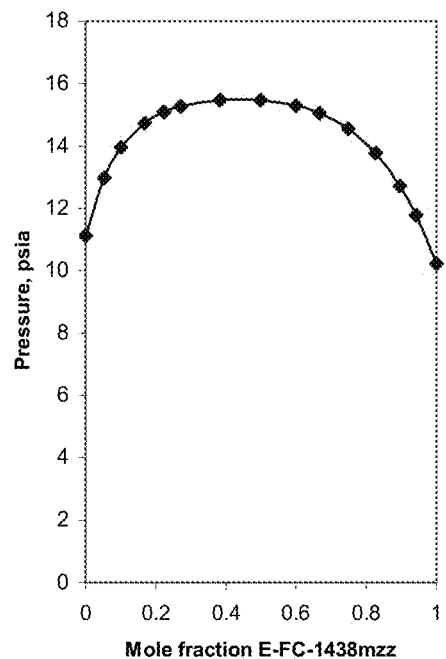

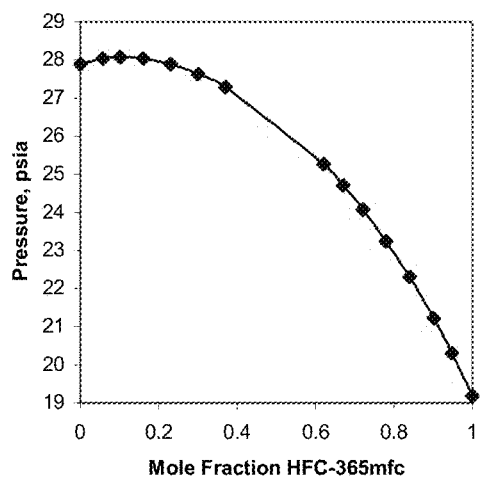

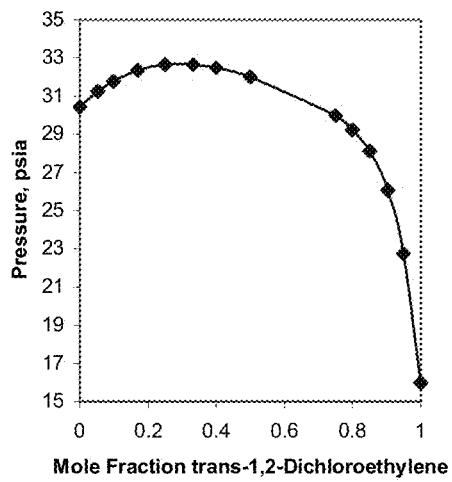

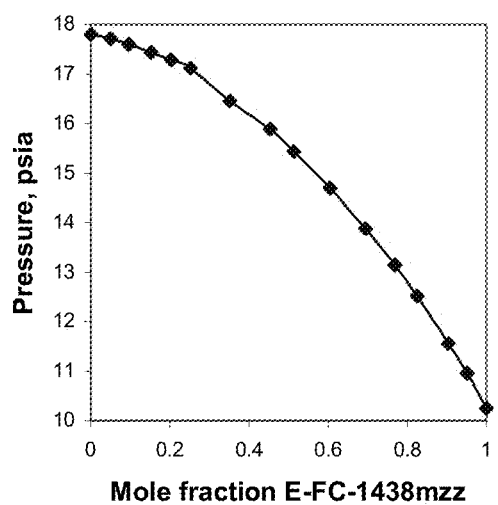

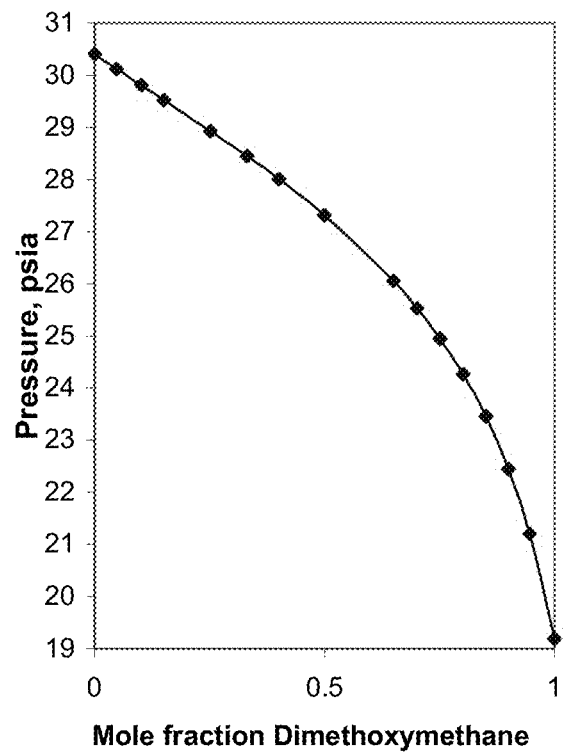

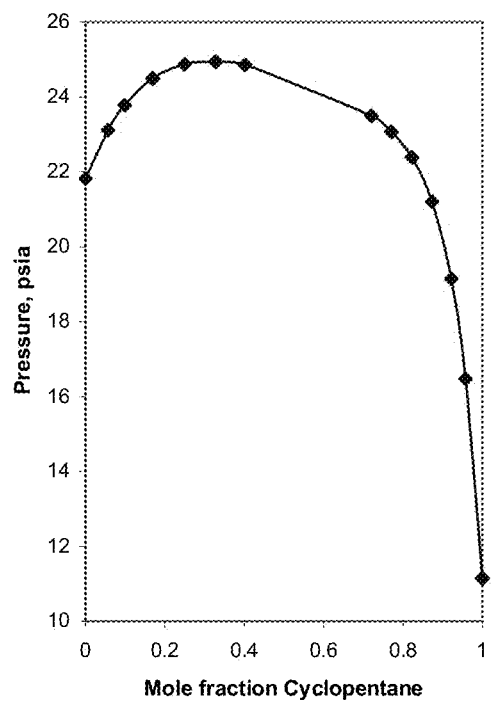

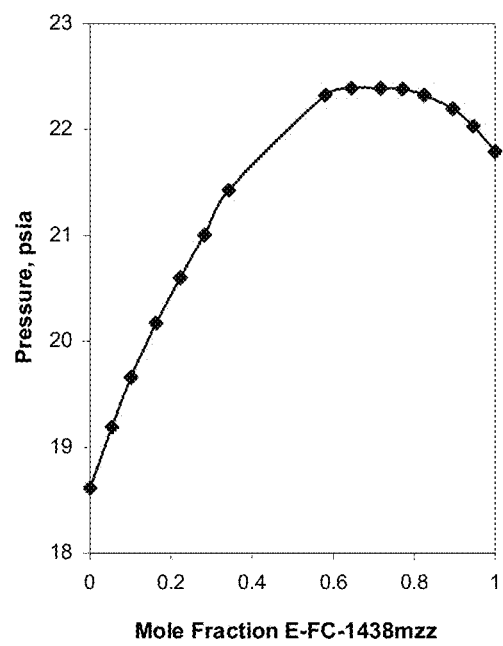

AZEOTROPIC AND AZEOTROPE-LIKE COMPOSITIONS OF E-1,1,1,4,4,5,5,5-OCTAFLUORO-2-PENTENE

This application claims priority of U.S. Patent Application 60/970,393 filed Sep. 6, 2007, U.S. Patent Application 60/993,254 and 60/993,240 filed Sep. 11, 2007, U.S. Patent Application 61/012,846 and 61/012,848 filed Dec. 11, 2007, U.S. Patent Application 61/021,132, 61/021,139 and 61/021,145 filed Jan. 15, 2008.

BACKGROUND OF THE INVENTION

1. Field of the Disclosure

The present disclosure relates to azeotropic or azeotrope-like compositions of E-1,1,1,4,4,5,5,5-Octafluoro-2-pentene.

2. Description of Related Art

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for compositions that do not contribute to the destruction of stratospheric ozone and also have low global warming potentials (GWPs). Certain hydrofluoroolefins, such as E-1,1,1,4,4,5,5,5-Octafluoro-2-pentene (E-$CF_3CH=CHCF_2CF_3$, E-FC-1438mzz, trans-FC-1438mzz) are believed to meet both goals.

SUMMARY OF THE INVENTION

This application includes nine different types of azeotropic or azeotrope-like mixtures.

This disclosure provides a composition consisting essentially of (a) E-FC-1438mzz and (b) methyl formate; wherein the methyl formate is present in an effective amount to form an azeotropic or azeotrope-like mixture with E-FC-1438mzz.

This disclosure also provides a composition consisting essentially of (a) E-FC-1438mzz and (b) n-pentane; wherein the n-pentane is present in an effective amount to form an azeotropic or azeotrope-like mixture with E-FC-1438mzz.

This disclosure also provides a composition consisting essentially of (a) E-FC-1438mzz and (b) 2-methylbutane (isopentane); wherein the isopentane is present in an effective amount to form an azeotropic or azeotrope-like mixture with E-FC-1438mzz.

This disclosure also provides a composition consisting essentially of (a) E-FC-1438mzz and (b) 1,1,1,3,3-pentafluorobutane ($CF_3CH_2CF_2CH_3$, HFC-365mfc); wherein the HFC-365mfc is present in an effective amount to form an azeotropic or azeotrope-like mixture with E-FC-1438mzz.

This disclosure also provides a composition consisting essentially of (a) E-FC-1438mzz and (b) trans-1,2-dichloroethylene; wherein the trans-1,2-dichloroethylene is present in an effective amount to form an azeotropic or azeotrope-like mixture with E-FC-1438mzz.

This disclosure also provides a composition consisting essentially of (a) E-FC-1438mzz and (b) 1,1,1,3,3-pentafluoropropane ($CF_3CH_2CF_2H$, HFC-245fa); wherein the HFC-245fa is present in an effective amount to form an azeotrope-like mixture with E-FC-1438mzz.

This disclosure also provides a composition consisting essentially of (a) E-FC-1438mzz and (b) dimethoxymethane ($CH_3OCH_2OCH_3$, methylal); wherein the dimethoxymethane is present in an effective amount to form an azeotrope-like mixture with E-FC-1438mzz.

This disclosure also provides a composition consisting essentially of (a) E-FC-1438mzz and (b) cyclopentane (c-$C_5H_{10}$); wherein the cyclopentane is present in an effective amount to form an azeotropic or azeotrope-like mixture with E-FC-1438mzz.

This disclosure also provides a composition consisting essentially of (a) E-FC-1438mzz and (b) Z-1,1,1,4,4,4-hexafluoro-2-butene (Z-$CF_3CH=CHCF_3$, Z-FC-1336mzz, cis-FC-1336mzz); wherein the Z-FC-1336mzz is present in an effective amount to form an azeotropic or azeotrope-like mixture with E-FC-1438mzz.

BRIEF SUMMARY OF THE DRAWINGS

FIG. 1 is a graphical representation of an azeotrope and azeotrope-like compositions consisting essentially of E-FC-1438mzz and methyl formate at a temperature of about 34.9° C.

FIG. 2 is a graphical representation of an azeotrope and azeotrope-like compositions consisting essentially of E-FC-1438mzz and n-pentane at a temperature of about 39.9° C.

FIG. 3 is a graphical representation of an azeotrope and azeotrope-like compositions consisting essentially of E-FC-1438mzz and isopentane at a temperature of about 20.0° C.

FIG. 4 is a graphical representation of an azeotrope and azeotrope-like compositions consisting essentially of E-FC-1438mzz and HFC-365mfc at a temperature of about 47.6° C.

FIG. 5 is a graphical representation of an azeotrope and azeotrope-like compositions consisting essentially of E-FC-1438mzz and trans-1,2-dichloroethylene at a temperature of about 50.0° C.

FIG. 6 is a graphical representation of azeotrope-like compositions consisting essentially of E-FC-1438mzz and HFC-245fa at a temperature of about 20.0° C.

FIG. 7 is a graphical representation of azeotrope-like compositions consisting essentially of E-FC-1438mzz and dimethoxymethane at a temperature of about 50.0° C.

FIG. 8 is a graphical representation of an azeotrope and azeotrope-like compositions consisting essentially of E-FC-1438mzz and cyclopentane at a temperature of about 39.9° C.

FIG. 9 is a graphical representation of an azeotrope and azeotrope-like compositions consisting essentially of E-FC-1438mzz and Z-FC-1336mzz at a temperature of about 40.0° C.

DETAILED DESCRIPTION OF THE INVENTION

In many applications, the use of a pure single component or an azeotropic or azeotrope-like mixture is desirable. For example, when a blowing agent composition (also known as foam expansion agents or foam expansion compositions) is not a pure single component or an azeotropic or azeotrope-like mixture, the composition may change during its application in the foam forming process. Such change in composition could detrimentally affect processing or cause poor performance in the application. Also, in refrigeration applications, a refrigerant is often lost during operation through leaks in shaft seals, hose connections, soldered joints and broken lines. In addition, the refrigerant may be released to the atmosphere during maintenance procedures on refrigeration equipment. If the refrigerant is not a pure single component or an azeotropic or azeotrope-like composition, the refrigerant composition may change when leaked or discharged to the atmosphere from the refrigeration equipment. The change in refrigerant composition may cause the refrigerant to become flammable or to have poor refrigeration performance. Accordingly, there is a need for using azeotropic or azeotrope-like mixtures in these and other applications, for example azeotropic or azeotrope-like mixtures containing E-1,1,1,4,4,5,5,5-Octafluoro-2-pentene (E-CF$_3$CH=CHCF$_2$CF$_3$, E-FC-1438mzz, trans-FC-1438mzz).

Before addressing details of embodiments described below, some terms are defined or clarified.

FC-1438mzz may exist as one of two configurational isomers, E or Z. FC-1438mzz as used herein refers to the isomers, Z-FC-1438mzz or E-FC-1438mzz, as well as any combinations or mixtures of such isomers.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

E-FC-1438mzz is a known compound, and its preparation method has been disclosed, for example, in Patent Application Publication WO 2008/0575313 A1, hereby incorporated by reference in its entirety.

This application includes azeotropic or azeotrope-like compositions comprising E-FC-1438mzz.

In some embodiments of this invention, the composition consists essentially of (a) E-FC-1438mzz and (b) methyl formate; wherein the methyl formate is present in an effective amount to form an azeotropic or azeotrope-like mixture with E-FC-1438mzz.

In some embodiments of this invention, the composition consists essentially of (a) E-FC-1438mzz and (b) n-pentane; wherein the n-pentane is present in an effective amount to form an azeotropic or azeotrope-like mixture with E-FC-1438mzz.

In some embodiments of this invention, the composition consists essentially of (a) E-FC-1438mzz and (b) isopentane; wherein the isopentane is present in an effective amount to form an azeotropic or azeotrope-like mixture with E-FC-1438mzz.

In some embodiments of this invention, the composition consists essentially of (a) E-FC-1438mzz and (b) HFC-365mfc; wherein the HFC-365mfc is present in an effective amount to form an azeotropic or azeotrope-like mixture with E-FC-1438mzz.

In some embodiments of this invention, the composition consists essentially of (a) E-FC-1438mzz and (b) trans-1,2-dichloroethylene; wherein the trans-1,2-dichloroethylene is present in an effective amount to form an azeotropic or azeotrope-like mixture with E-FC-1438mzz.

In some embodiments of this invention, the composition consists essentially of (a) E-FC-1438mzz and (b) HFC-245fa; wherein the HFC-245fa is present in an effective amount to form an azeotrope-like mixture with E-FC-1438mzz.

In some embodiments of this invention, the composition consists essentially of (a) E-FC-1438mzz and (b) dimethoxymethane; wherein the dimethoxymethane is present in an effective amount to form an azeotrope-like mixture with E-FC-1438mzz.

In some embodiments of this invention, the composition consists essentially of (a) E-FC-1438mzz and (b) cyclopentane; wherein the cyclopentane is present in an effective amount to form an azeotropic or azeotrope-like mixture with E-FC-1438mzz.

In some embodiments of this invention, the composition consists essentially of (a) E-FC-1438mzz and (b) Z-FC-1336mzz; wherein the Z-FC-1336mzz is present in an effective amount to form an azeotropic or azeotrope-like mixture with E-FC-1438mzz.

By effective amount is meant an amount, which, when combined with E-FC-1438mzz, results in the formation of an azeotropic or azeotrope-like mixture. This definition includes the amounts of each component, which amounts may vary depending on the pressure applied to the composition so long as the azeotropic or azeotrope-like compositions continue to exist at the different pressures, but with possible different boiling points. Therefore, effective amount includes the amounts, such as may be expressed in weight or mole percentages, of each component of the compositions of the instant invention which form azeotropic or azeotrope-like compositions at temperatures or pressures other than as described herein.

As recognized in the art, an azeotropic composition is an admixture of two or more different components which, when in liquid form under a given pressure, will boil at a substantially constant temperature, which temperature may be higher or lower than the boiling temperatures of the individual components, and which will provide a vapor composition essentially identical to the overall liquid composition undergoing boiling. (see, e.g., M. F. Doherty and M. F. Malone, Conceptual Design of Distillation Systems, McGraw-Hill (New York), 2001, 185-186, 351-359).

Accordingly, the essential features of an azeotropic composition are that at a given pressure, the boiling point of the liquid composition is fixed and that the composition of the vapor above the boiling composition is essentially that of the overall boiling liquid composition (i.e., no fractionation of the components of the liquid composition takes place). It is also recognized in the art that both the boiling point and the weight percentages of each component of the azeotropic composition may change when the azeotropic composition is subjected to boiling at different pressures. Thus, an azeotropic composition may be defined in terms of the unique relationship that exists among the components or in terms of the compositional ranges of the components or in terms of exact weight percentages of each component of the composition characterized by a fixed boiling point at a specified pressure.

For the purpose of this invention, an azeotrope-like composition means a composition that behaves like an azeotropic composition (i.e., has constant boiling characteristics or a tendency not to fractionate upon boiling or evaporation). Hence, during boiling or evaporation, the vapor and liquid compositions, if they change at all, change only to a minimal or negligible extent. This is to be contrasted with non-azeotrope-like compositions in which during boiling or evaporation, the vapor and liquid compositions change to a substantial degree.

Additionally, azeotrope-like compositions exhibit dew point pressure and bubble point pressure with virtually no pressure differential. That is to say that the difference in the dew point pressure and bubble point pressure at a given temperature will be a small value. In this invention, compositions with a difference in dew point pressure and bubble point pressure of less than or equal to 5 percent (based upon the bubble point pressure) is considered to be azeotrope-like.

It is recognized in this field that when the relative volatility of a system approaches 1.0, the system is defined as forming an azeotropic or azeotrope-like composition. Relative volatility is the ratio of the volatility of component 1 to the volatility of component 2. The ratio of the mole fraction of a component in vapor to that in liquid is the volatility of the component.

To determine the relative volatility of any two compounds, a method known as the PTx method can be used. In this procedure, the total absolute pressure in a cell of known volume is measured at a constant temperature for various compositions of the two compounds. Use of the PTx Method is described in detail in "Phase Equilibrium in Process Design", Wiley-Interscience Publisher, 1970, written by Harold R. Null, on pages 124 to 126; hereby incorporated by reference.

These measurements can be converted into equilibrium vapor and liquid compositions in the PTx cell by using an activity coefficient equation model, such as the Non-Random, Two-Liquid (NRTL) equation, to represent liquid phase non-idealities. Use of an activity coefficient equation, such as the NRTL equation is described in detail in "The Properties of Gases and Liquids," 4th edition, published by McGraw Hill, written by Reid, Prausnitz and Poling, on pages 241 to 387, and in "Phase Equilibria in Chemical Engineering," published by Butterworth Publishers, 1985, written by Stanley M. Walas, pages 165 to 244. Both aforementioned references are hereby incorporated by reference. Without wishing to be bound by any theory or explanation, it is believed that the NRTL equation, together with the PTx cell data, can sufficiently predict the relative volatilities of the E-1,1,1,4,4,5,5,5-Octafluoro-2-pentene-containing compositions of the present invention and can therefore predict the behavior of these mixtures in multi-stage separation equipment such as distillation columns.

It was found through experiments that E-FC-1438mzz and methyl formate form azeotropic or azeotrope-like compositions.

To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/methyl formate mixtures is shown in FIG. 1, which graphically illustrates the formation of an azeotropic and azeotrope-like compositions consisting essentially of E-FC-1438mzz and methyl formate as indicated by a mixture of about 41.2 mole % (71.4 weight %) E-FC-1438mzz and 58.8 mole % (28.6 weight %) methyl formate having the highest pressure over the range of compositions at this temperature. Based upon these findings, it has been calculated that E-FC-1438mzz and methyl formate form azeotropic compositions ranging from about 39.3 mole percent (69.8 weight percent) to about 41.4 mole percent (71.5 weight percent) E-FC-1438mzz and from about 58.6 mole percent (28.5 weight percent) to about 60.7 mole percent (30.2 weight percent) methyl formate (which form azeotropic compositions boiling at a temperature of from about −30° C. to about 140° C. and at a pressure of from about 1.0 psia (7 kPa) to about 299 psia (2062 kPa)). Some embodiments of azeotropic compositions are listed in Table 1.

TABLE 1

Azeotropic compositions

| Azeotropic Temperature (° C.) | Azeotropic Pressure (psia) | E-FC-1438mzz (mole %) | Methyl formate (mole %) |
|---|---|---|---|
| −20.0 | 1.82 | 39.8 | 60.2 |
| 0.0 | 5.15 | 40.6 | 59.4 |
| 20.0 | 12.3 | 41.0 | 59.0 |
| 40.0 | 25.6 | 41.2 | 58.8 |
| 60.0 | 47.9 | 41.2 | 58.8 |
| 80.0 | 82.7 | 41.1 | 58.9 |
| 100.0 | 133.5 | 41.1 | 58.9 |
| 120.0 | 204.1 | 41.1 | 58.9 |
| 140.0 | 298.6 | 41.4 | 58.6 |

Additionally, azeotrope-like compositions containing E-FC-1438mzz and methyl formate may also be formed. Such azeotrope-like compositions exist around azeotropic compositions. Some embodiments of azeotrope-like compositions are listed in Table 2. Additional embodiments of azeotrope-like compositions are listed in Table 3.

TABLE 2

Azeotrope-like compositions

| COMPONENTS | T (° C.) | Weight Percentage Range |
|---|---|---|
| E-FC-1438mzz/Methyl formate | −20 | 58-99/1-42 |
| E-FC-1438mzz/Methyl formate | 20 | 53-99/1-47 |
| E-FC-1438mzz/Methyl formate | 40 | 50-99/1-50 |
| E-FC-1438mzz/Methyl formate | 60 | 45-99/1-55 |
| E-FC-1438mzz/Methyl formate | 100 | 1-99/1-99 |
| E-FC-1438mzz/Methyl formate | 140 | 1-99/1-99 |

TABLE 3

Azeotrope-like compositions

| COMPONENTS | T (° C.) | Weight Percentage Range |
|---|---|---|
| E-FC-1438mzz/Methyl formate | −20 | 60-85/15-40 |
| E-FC-1438mzz/Methyl formate | 20 | 58-90/10-42 |
| E-FC-1438mzz/Methyl formate | 40 | 56-90/10-44 |
| E-FC-1438mzz/Methyl formate | 60 | 53-90/10-47 |
| E-FC-1438mzz/Methyl formate | 100 | 10-90/10-90 |
| E-FC-1438mzz/Methyl formate | 140 | 10-90/10-90 |

It was found through experiments that E-FC-1438mzz and n-pentane form azeotropic or azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/n-pentane mixtures is shown in FIG. 2, which illustrates graphically the formation of an azeotropic and azeotrope-like compositions consisting essentially of E-FC-1438mzz and n-pentane at 39.9° C., as indicated by a mixture of about 56.9 mole % (79.7 weight %) E-FC-1438mzz and 43.1 mole % (20.3 weight %) n-pentane having the highest pressure over the range of compositions at this temperature.

Based upon these findings, it has been calculated that E-FC-1438mzz and n-pentane form azeotropic compositions ranging from about 48.6 mole percent (73.7 weight percent) to about 66.8 mole percent (85.7 weight percent) E-FC-1438mzz and from about 33.2 mole percent (14.3 weight percent) to about 51.4 mole percent (26.3 weight percent) n-pentane (which form azeotropic compositions boiling at a temperature of from about −40° C. to about 130° C. and at a pressure of from about 0.6 psia (4 kPa) to about 251 psia (1730 kPa)). Some embodiments of azeotropic compositions are listed in Table 4.

TABLE 4

Azeotropic compositions

| Azeotropic Temperature (° C.) | Azeotropic Pressure (psia) | E-FC-1438mzz (mole %) | n-Pentane (mole %) |
|---|---|---|---|
| −40 | 0.6 | 48.6 | 51.4 |
| −20 | 2.2 | 51.2 | 48.8 |
| 0.0 | 6.0 | 53.4 | 46.6 |
| 20.0 | 13.8 | 55.2 | 44.8 |
| 40.0 | 27.9 | 56.9 | 43.1 |
| 60.0 | 50.9 | 58.7 | 41.3 |
| 80.0 | 85.8 | 60.7 | 39.3 |
| 100.0 | 136.1 | 62.9 | 37.1 |
| 120.0 | 206.0 | 65.5 | 34.5 |

Additionally, azeotrope-like compositions containing E-FC-1438mzz and n-pentane may also be formed. Such azeotrope-like compositions exist around azeotropic compositions. Some embodiments of azeotrope-like compositions are listed in Table 5. Additional embodiments of azeotrope-like compositions are listed in Table 6.

TABLE 5

Azeotrope-like compositions

| COMPONENTS | T (° C.) | Weight Percentage Range |
|---|---|---|
| E-FC-1438mzz/n-Pentane | −20 | 69-83/17-31 |
| E-FC-1438mzz/n-Pentane | 20 | 70-88/12-30 |
| E-FC-1438mzz/n-Pentane | 40 | 70-91/10-29 |
| E-FC-1438mzz/n-Pentane | 60 | 70-99/1-30 |
| E-FC-1438mzz/n-Pentane | 100 | 68-99/1-32 |
| E-FC-1438mzz/n-Pentane | 130 | 65-99/1-35 |

TABLE 6

Azeotrope-like compositions

| COMPONENTS | T (° C.) | Weight Percentage Range |
|---|---|---|
| E-FC-1438mzz/n-Pentane | −20 | 71-81/19-29 |
| E-FC-1438mzz/n-Pentane | 20 | 72-85/15-28 |
| E-FC-1438mzz/n-Pentane | 40 | 72-88/12-28 |
| E-FC-1438mzz/n-Pentane | 60 | 72-90/10-28 |
| E-FC-1438mzz/n-Pentane | 100 | 72-90/10-28 |
| E-FC-1438mzz/n-Pentane | 130 | 71-90/10-29 |

It was found through experiments that E-FC-1438mzz and isopentane form azeotropic or azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/isopentane mixtures is shown in FIG. 3, which illustrates graphically the formation of an azeotrope and azeotrope-like compositions of E-FC-1438mzz and isopentane at 20.0° C., as indicated by a mixture of about 44.1 mole % (70.1 weight %) E-FC-1438mzz and 55.9 mole % (29.9 weight %) isopentane having the highest pressure over the range of compositions at this temperature.

Based upon these findings, it has been calculated that E-FC-1438mzz and isopentane form azeotropic compositions ranging from about 34.7 mole percent (61.2 weight percent) to about 58.9 mole percent (80.9 weight percent) E-FC-1438mzz and from about 41.1 mole percent (19.1 weight percent) to about 65.3 mole percent (38.8 weight percent) isopentane (which form azeotropic compositions boiling at a temperature of from about −40° C. to about 130° C. and at a pressure of from about 0.8 psia (5.5 kPa) to about 262 psia (1806 kPa)). Some embodiments of azeotropic compositions are listed in Table 7.

TABLE 7

Azeotropic compositions

| Azeotropic Temperature (° C.) | Azeotropic Pressure (psia) | E-FC-1438mzz (mole %) | Isopentane (mole %) |
|---|---|---|---|
| −40.0 | 0.8 | 34.7 | 65.3 |
| −20.0 | 2.7 | 38.4 | 61.6 |
| 0.0 | 7.0 | 41.4 | 58.6 |
| 20.0 | 15.5 | 44.1 | 55.9 |
| 40.0 | 30.6 | 46.5 | 53.5 |
| 60.0 | 54.8 | 48.9 | 51.1 |
| 80.0 | 91.2 | 51.3 | 48.7 |

TABLE 7-continued

Azeotropic compositions

| Azeotropic Temperature (° C.) | Azeotropic Pressure (psia) | E-FC-1438mzz (mole %) | Isopentane (mole %) |
|---|---|---|---|
| 100.0 | 143 | 54.0 | 46.0 |
| 120.0 | 216 | 57.1 | 42.9 |

Additionally, azeotrope-like compositions containing E-FC-1438mzz and isopentane may also be formed. Such azeotrope-like compositions exist around azeotropic compositions. Some embodiments of azeotrope-like compositions are listed in Table 8. Additional embodiments of azeotrope-like compositions are listed in Table 9.

TABLE 8

Azeotrope-like compositions

| COMPONENTS | T (° C.) | Weight Percentage Range |
|---|---|---|
| E-FC-1438mzz/Isopentane | −40 | 52-68/32-48 |
| E-FC-1438mzz/Isopentane | 0 | 57-77/23-43 |
| E-FC-1438mzz/Isopentane | 40 | 58-84/16-42 |
| E-FC-1438mzz/Isopentane | 80 | 56-99/1-44 |
| E-FC-1438mzz/Isopentane | 120 | 49-99/1-51 |

TABLE 9

Azeotrope-like compositions

| COMPONENTS | T (° C.) | Weight Percentage Range |
|---|---|---|
| E-FC-1438mzz/Isopentane | −40 | 55-66/34-45 |
| E-FC-1438mzz/Isopentane | 0 | 60-75/25-40 |
| E-FC-1438mzz/Isopentane | 40 | 62-81/19-38 |
| E-FC-1438mzz/Isopentane | 80 | 62-89/11-38 |
| E-FC-1438mzz/Isopentane | 120 | 60-90/10-40 |

It was found through experiments that E-FC-1438mzz and HFC-365mfc form azeotropic and azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/HFC-365mfc mixtures is shown in FIG. 4, which illustrates graphically the formation of an azeotrope and azeotrope-like compositions of E-FC-1438mzz and HFC-365mfc at 47.6° C., as indicated by a mixture of about 90.6 mole % (93.3 weight %) E-FC-1438mzz and 9.4 mole % (6.7 weight %) HFC-365mfc having the highest pressure at this temperature.

Based upon these findings, it has been calculated that E-FC-1438mzz and HFC-365mfc form azeotropic compositions ranging from about 82.6 mole percent (87.3 weight percent) to about 98.2 mole percent (98.8 weight percent) E-FC-1438mzz and from about 1.8 mole percent (1.2 weight percent) to about 17.4 mole percent (12.7 weight percent) HFC-365mfc (which form azeotropic compositions boiling at a temperature of from about −20° C. to about 130° C. and at a pressure of from about 1.5 psia (10 kPa) to about 228 psia (1572 kPa)). Some embodiments of azeotropic compositions are listed in Table 10.

TABLE 10

Azeotropic compositions

| Azeotropic Temperature (° C.) | Azeotropic Pressure (psia) | E-FC-1438mzz (mole %) | HFC-365mfc (mole %) |
|---|---|---|---|
| −20.0 | 1.5 | 82.6 | 17.4 |
| 0.0 | 4.3 | 85.4 | 14.6 |
| 20.0 | 10.4 | 87.8 | 12.2 |
| 40.0 | 22.0 | 89.8 | 10.2 |
| 60.0 | 41.8 | 91.7 | 8.3 |
| 80.0 | 73.2 | 93.6 | 6.4 |
| 100.0 | 119.8 | 95.7 | 4.3 |
| 120.0 | 186.1 | 97.7 | 2.3 |

Additionally, azeotrope-like compositions containing E-FC-1438mzz and HFC-365mfc may also be formed. Such azeotrope-like compositions exist around azeotropic compositions. Some embodiments of azeotrope-like compositions are listed in Table 11. Additional embodiments of azeotrope-like compositions are listed in Table 12.

TABLE 11

Azeotrope-like compositions

| COMPONENTS | T (° C.) | Weight Percentage Range |
|---|---|---|
| E-FC-1438mzz/HFC-365mfc | −20 | 65-99/1-35 |
| E-FC-1438mzz/HFC-365mfc | 20 | 61-99/1-39 |
| E-FC-1438mzz/HFC-365mfc | 40 | 56-99/1-44 |
| E-FC-1438mzz/HFC-365mfc | 60 | 50-99/1-50 |
| E-FC-1438mzz/HFC-365mfc | 100 | 1-99/1-99 |
| E-FC-1438mzz/HFC-365mfc | 140 | 1-99/1-99 |

TABLE 12

Azeotrope-like compositions

| COMPONENTS | T (° C.) | Weight Percentage Range |
|---|---|---|
| E-FC-1438mzz/HFC-365mfc | −20 | 70-90/10-30 |
| E-FC-1438mzz/HFC-365mfc | 20 | 68-90/10-32 |
| E-FC-1438mzz/HFC-365mfc | 40 | 66-90/10-34 |
| E-FC-1438mzz/HFC-365mfc | 60 | 63-90/10-37 |
| E-FC-1438mzz/HFC-365mfc | 100 | 55-90/10-45 |
| E-FC-1438mzz/HFC-365mfc | 140 | 10-90/10-90 |

It was found through experiments that E-FC-1438mzz and trans-1,2-dichloroethylene form azeotropic or azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/trans-1,2-dichloroethylene mixtures is shown in FIG. 5, which illustrates graphically the formation of an azeotropic and azeotrope-like compositions of E-FC-1438mzz and trans-1,2-dichloroethylene at 50.0° C., as indicated by a mixture of about 71.4 mole % (84.6 weight %) E-FC-1438mzz and 28.6 mole % (15.4 weight %) trans-1,2-dichloroethylene having the highest pressure over the range of compositions at this temperature.

Based upon these findings, it has been calculated that E-FC-1438mzz and trans-1,2-dichloroethylene form azeotropic compositions ranging from about 65.2 mole percent (80.6 weight percent) to about 87.8 mole percent (94.1 weight percent) E-FC-1438mzz and from about 12.2 mole percent (5.9 weight percent) to about 34.8 mole percent (19.4 weight percent) trans-1,2-dichloroethylene (which form azeotropic compositions boiling at a temperature of from about −20° C. to about 140° C. and at a pressure of from about 1.7 psia (12 kPa) to about 280 psia (1930 kPa)). Some embodiments of azeotropic compositions are listed in Table 13.

TABLE 13

Azeotropic compositions

| Azeotropic Temperature (° C.) | Azeotropic Pressure (psia) | E-FC-1438mzz (mole %) | trans-1,2-dichloroethylene (mole %) |
|---|---|---|---|
| −20.0 | 1.7 | 65.2 | 34.8 |
| 0.0 | 4.8 | 66.4 | 33.6 |
| 20.0 | 11.4 | 68.0 | 32.0 |
| 40.0 | 23.7 | 70.1 | 29.9 |
| 60.0 | 44.2 | 72.8 | 27.2 |
| 80.0 | 76.1 | 75.8 | 24.2 |
| 100.0 | 122.9 | 79.5 | 20.5 |
| 120.0 | 189.1 | 83.6 | 16.4 |
| 140.0 | 280.3 | 87.8 | 12.2 |

Additionally, azeotrope-like compositions containing E-FC-1438mzz and trans-1,2-dichloroethylene may also be formed. Such azeotrope-like compositions exist around azeotropic compositions. Some embodiments of azeotrope-like compositions are listed in Table 14. Additional embodiments of azeotrope-like compositions are listed in Table 15.

TABLE 14

Azeotrope-like compositions

| COMPONENTS | T (° C.) | Weight Percentage Range |
|---|---|---|
| E-FC-1438mzz/trans-1,2-dichloroethylene | −20 | 75-99/1-25 |
| E-FC-1438mzz/trans-1,2-dichloroethylene | 20 | 73-99/1-27 |
| E-FC-1438mzz/trans-1,2-dichloroethylene | 40 | 73-99/1-27 |
| E-FC-1438mzz/trans-1,2-dichloroethylene | 60 | 72-99/1-28 |
| E-FC-1438mzz/trans-1,2-dichloroethylene | 100 | 71-99/1-29 |
| E-FC-1438mzz/trans-1,2-dichloroethylene | 140 | 69-99/1-31 |

TABLE 15

Azeotrope-like compositions

| COMPONENTS | T (° C.) | Weight Percentage Range |
|---|---|---|
| E-FC-1438mzz/trans-1,2-dichloroethylene | −20 | 76-90/10-24 |
| E-FC-1438mzz/trans-1,2-dichloroethylene | 20 | 75-90/10-25 |
| E-FC-1438mzz/trans-1,2-dichloroethylene | 40 | 75-90/10-25 |
| E-FC-1438mzz/trans-1,2-dichloroethylene | 60 | 75-90/10-25 |
| E-FC-1438mzz/trans-1,2-dichloroethylene | 100 | 75-90/10-25 |
| E-FC-1438mzz/trans-1,2-dichloroethylene | 140 | 74-90/10-26 |

It was found through experiments that E-FC-1438mzz and HFC-245fa form azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/HFC-245fa mixtures is shown in FIG. 6, which illustrates graphically the formation of azeotrope-like compositions of E-FC-1438mzz and HFC-245fa at 20.0° C., as indicated by mixtures of about 1 to 36 mole % (1 to 47 weight %) E-FC-1438mzz and about 64 to 99 mole % (53 to 99 weight %) HFC-245fa with vapor pressure of approximately 17 psia (117 kPa), and by mixtures of about 91 to 99 mole percent (94 to 99 weight %) E-FC-1438mzz and 1 to 9 mole % (1 to 6 weight %) HFC-245fa with vapor pressure of approximately 11 psia (76 kPa).

Some embodiments of azeotrope-like compositions are listed in Table 16. Additional embodiments of azeotrope-like compositions are listed in Table 17.

TABLE 16

Azeotrope-like compositions

| COMPONENTS | T (° C.) | Weight Percentage Range |
|---|---|---|
| E-FC-1438mzz/HFC-245fa | −40 | 1-35/65-99 and 98-99/1-2 |
| E-FC-1438mzz/HFC-245fa | 0 | 1-42/58-99 and 96-99/1-4 |
| E-FC-1438mzz/HFC-245fa | 20 | 1-47/53-99 and 94-99/1-6 |
| E-FC-1438mzz/HFC-245fa | 40 | 1-51/49-99 and 93-99/1-7 |
| E-FC-1438mzz/HFC-245fa | 80 | 1-68/32-99 and 83-99/1-17 |
| E-FC-1438mzz/HFC-245fa | 120 | 1-99/1-99 |

TABLE 17

Azeotrope-like compositions

| COMPONENTS | T (° C.) | Weight Percentage Range |
|---|---|---|
| E-FC-1438mzz/HFC-245fa | −40 | 5-10/90-95 |
| E-FC-1438mzz/HFC-245fa | 0 | 10-34/66-90 |
| E-FC-1438mzz/HFC-245fa | 20 | 10-37/63-90 |
| E-FC-1438mzz/HFC-245fa | 40 | 10-40/60-90 |
| E-FC-1438mzz/HFC-245fa | 80 | 10-48/52-90 |
| E-FC-1438mzz/HFC-245fa | 120 | 5-95/5-95 |

It was found through experiments that E-FC-1438mzz and dimethoxymethane form azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/dimethoxymethane mixtures is shown in FIG. 7, which illustrates graphically the formation of azeotrope-like compositions of E-FC-1438mzz and dimethoxymethane at 50.0° C. and about 20 psia (138 kPa), as indicated by mixtures of about 1 to 4 mole % (3 to 11 weight %) E-FC-1438mzz and about 96 to 99 mole % (89 to 97 weight %) dimethoxymethane, and azeotrope-like compositions of E-FC-1438mzz and dimethoxymethane at 50.0° C. and about 28 psia (193 kPa), as indicated by mixtures of about 37 to 99 mole % (62 to 99 weight %) E-FC-1438mzz and about 1 to 63 mole % (1 to 38 weight %) dimethoxymethane.

Some embodiments of azeotrope-like compositions are listed in Table 18. Additional embodiments of azeotrope-like compositions are listed in Table 19.

TABLE 18

Azeotrope-like compositions

| COMPONENTS | T (° C.) | Weight Percentage Range |
|---|---|---|
| E-FC-1438mzz/Dimethoxymethane | −40 | 71-99/1-29 |
| E-FC-1438mzz/Dimethoxymethane | 0 | 1-6/94-99 and 69-99/1-31 |
| E-FC-1438mzz/Dimethoxymethane | 40 | 1-9/91-99 and 64-99/1-36 |
| E-FC-1438mzz/Dimethoxymethane | 80 | 1-18/82-99 and 54-99/1-46 |
| E-FC-1438mzz/Dimethoxymethane | 120 | 1-99/1-99 |
| E-FC-1438mzz/Dimethoxymethane | 150 | 1-99/1-99 |

TABLE 19

Azeotrope-like compositions

| COMPONENTS | T (° C.) | Weight Percentage Range |
|---|---|---|
| E-FC-1438mzz/Dimethoxymethane | −40 | 77-90/10-23 |
| E-FC-1438mzz/Dimethoxymethane | 0 | 76-90/10-24 |
| E-FC-1438mzz/Dimethoxymethane | 40 | 73-90/10-27 |
| E-FC-1438mzz/Dimethoxymethane | 80 | 68-90/10-32 |
| E-FC-1438mzz/Dimethoxymethane | 120 | 10-17/83-90 and 59-90/10-41 |
| E-FC-1438mzz/Dimethoxymethane | 150 | 10-90/10-90 |

It was found through experiments that E-FC-1438mzz and cyclopentane form azeotropic or azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/cyclopentane mixture is shown in FIG. 8, which illustrates graphically the formation of an azeotropic and azeotrope-like compositions of E-FC-1438mzz and cyclopentane at 39.9° C., as indicated by a mixture of about 70.0 mole % (87.7 weight %) E-FC-1438mzz and 30.0 mole % (12.3 weight %) cyclopentane having the highest pressure over the range of compositions at this temperature.

Based upon these findings, it has been calculated that E-FC-1438mzz and cyclopentane form azeotropic compositions ranging from about 65.5 mole percent (85.3 weight percent) to about 85.4 mole percent (94.7 weight percent) E-FC-1438mzz and from about 14.6 mole percent (5.3 weight percent) to about 34.5 mole percent (14.7 weight percent) cyclopentane (which form azeotropic compositions boiling at a temperature of from about −40° C. to about 140° C. and at a pressure of from about 0.5 psia (3.5 kPa) to about 283 psia (1951 kPa)). Some embodiments of azeotropic compositions are listed in Table 20.

TABLE 20

Azeotropic compositions

| Azeotropic Temperature (° C.) | Azeotropic Pressure (psia) | E-FC-1438mzz (mole %) | Cyclopentane (mole %) |
|---|---|---|---|
| −40.0 | 0.5 | 65.5 | 34.5 |
| −20.0 | 1.8 | 66.4 | 33.6 |
| 0.0 | 5.1 | 67.4 | 32.6 |
| 20.0 | 12.0 | 68.6 | 31.4 |
| 40.0 | 24.7 | 70.0 | 30.0 |
| 60.0 | 45.8 | 71.8 | 28.2 |
| 80.0 | 78.3 | 74.1 | 25.9 |
| 100.0 | 125.5 | 77.0 | 23.0 |
| 120.0 | 191.7 | 81.0 | 19.0 |
| 140.0 | 282.7 | 85.4 | 14.6 |

Additionally, azeotrope-like compositions containing E-FC-1438mzz and cyclopentane may also be formed. Such azeotrope-like compositions exist around azeotropic compositions. Some embodiments of azeotrope-like compositions are listed in Table 21. Additional embodiments of azeotrope-like compositions are listed in Table 22.

TABLE 21

Azeotrope-like compositions

| COMPONENTS | T (° C.) | Weight Percentage Range |
|---|---|---|
| E-FC-1438mzz/cyclopentane | −20 | 82-92/8-18 |
| E-FC-1438mzz/cyclopentane | 20 | 82-99/1-18 |
| E-FC-1438mzz/cyclopentane | 40 | 81-99/1-19 |
| E-FC-1438mzz/cyclopentane | 60 | 80-99/1-20 |
| E-FC-1438mzz/cyclopentane | 100 | 79-99/1-21 |
| E-FC-1438mzz/cyclopentane | 140 | 78-99/1-22 |

TABLE 22

Azeotrope-like compositions

| COMPONENTS | T (° C.) | Weight Percentage Range |
|---|---|---|
| E-FC-1438mzz/cyclopentane | −20 | 83-90/10-17 |
| E-FC-1438mzz/cyclopentane | 20 | 82-90/10-18 |
| E-FC-1438mzz/cyclopentane | 40 | 82-90/10-18 |
| E-FC-1438mzz/cyclopentane | 60 | 82-90/10-18 |
| E-FC-1438mzz/cyclopentane | 100 | 82-90/10-18 |
| E-FC-1438mzz/cyclopentane | 140 | 82-90/10-18 |

It was found through experiments that E-FC-1438mzz and Z-FC-1336mzz form azeotropic or azeotrope-like compositions. To determine the relative volatility of this binary pair, the PTx method described above was used. The total absolute pressure in a PTx cell of known volume was measured at constant temperature for various binary compositions. These measurements were then reduced to equilibrium vapor and liquid compositions in the cell using the NRTL equation.

The vapor pressure measured versus the compositions in the PTx cell for E-FC-1438mzz/Z-FC-1336mzz mixtures is shown in FIG. 9, which illustrates graphically the formation of an azeotropic and azeotrope-like compositions of E-FC-1438mzz and Z-FC-1336mzz at 40.0° C., as indicated by a mixture of about 73.8 mole % (78.6 weight %) E-FC-1438mzz and 26.2 mole % (21.4 weight %) Z-FC-1336mzz having the highest pressure over the range of compositions at this temperature.

Based upon these findings, it has been calculated that E-FC-1438mzz and Z-FC-1336mzz form azeotropic compositions ranging from about 58.6 mole percent (64.8 weight percent) to about 82.5 mole percent (86.0 weight percent) E-FC-1438mzz and from about 17.5 mole percent (14.0 weight percent) to about 41.4 mole percent (35.2 weight percent) Z-FC-1336mzz (which form azeotropic compositions boiling at a temperature of from about −50° C. to about 140° C. and at a pressure of from about 0.2 psia (1.4 kPa) to about 281 psia (1937 kPa)). Some embodiments of azeotropic compositions are listed in Table 23.

TABLE 23

Azeotropic compositions

| Azeotropic Temperature (° C.) | Azeotropic Pressure (psia) | E-FC-1438mzz (mole %) | Z-FC-1336mzz (mole %) |
|---|---|---|---|
| −40.0 | 0.4 | 60.6 | 39.4 |
| −20.0 | 1.5 | 64.4 | 35.6 |
| 0.0 | 4.4 | 67.9 | 32.1 |
| 20.0 | 10.7 | 71.0 | 29.0 |
| 40.0 | 22.5 | 73.8 | 26.2 |
| 60.0 | 42.6 | 76.4 | 23.6 |
| 80.0 | 74.2 | 78.7 | 21.3 |
| 100.0 | 121.1 | 80.9 | 19.1 |
| 120.0 | 187.9 | 82.5 | 17.5 |
| 140.0 | 280.7 | 82.5 | 17.5 |

Additionally, azeotrope-like compositions containing E-FC-1438mzz and Z-FC-1336mzz may also be formed. Such azeotrope-like compositions exist around azeotropic compositions. Some embodiments of azeotrope-like compositions are listed in Table 24. Additional embodiments of azeotrope-like compositions are listed in Table 25.

TABLE 24

Azeotrope-like compositions

| COMPONENTS | T (° C.) | Weight Percentage Range |
|---|---|---|
| E-FC-1438mzz/Z-FC-1336mzz | −20 | 1-99/1-99 |
| E-FC-1438mzz/Z-FC-1336mzz | 20 | 1-99/1-99 |
| E-FC-1438mzz/Z-FC-1336mzz | 40 | 1-99/1-99 |
| E-FC-1438mzz/Z-FC-1336mzz | 60 | 1-99/1-99 |
| E-FC-1438mzz/Z-FC-1336mzz | 100 | 1-99/1-99 |
| E-FC-1438mzz/Z-FC-1336mzz | 140 | 1-99/1-99 |

TABLE 25

Azeotrope-like compositions

| COMPONENTS | T (° C.) | Weight Percentage Range |
|---|---|---|
| E-FC-1438mzz/Z-FC-1336mzz | −20 | 5-69/31-95 and 81-90/10-19 |
| E-FC-1438mzz/Z-FC-1336mzz | 20 | 10-90/10-90 |
| E-FC-1438mzz/Z-FC-1336mzz | 40 | 10-90/10-90 |
| E-FC-1438mzz/Z-FC-1336mzz | 60 | 10-90/10-90 |
| E-FC-1438mzz/Z-FC-1336mzz | 100 | 10-90/10-90 |
| E-FC-1438mzz/Z-FC-1336mzz | 140 | 10-90/10-90 |

The azeotropic or azeotrope-like compositions of the present invention can be prepared by any convenient method including mixing or combining the desired amounts. In one embodiment of this invention, an azeotropic or azeotrope-like composition can be prepared by weighing the desired component amounts and thereafter combining them in an appropriate container.

The azeotropic or azeotrope-like compositions of the present invention can be used in a wide range of applications, including their use as aerosol propellants, refrigerants, solvents, cleaning agents, blowing agents (foam expansion agents) for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. The azeotropic or azeotrope-like compositions of the present invention can also be used in purification methods, for example in distillation processes wherein the compositions of the present invention are employed to afford the separation of two or more compounds.

One embodiment of this invention provides a process for preparing a thermoplastic or thermoset foam. The process comprises using an azeotropic or azeotrope-like composition as a blowing agent, wherein said azeotropic or azeotrope-like composition consists essentially of E-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzzz.

Another embodiment of this invention provides a process for producing refrigeration. The process comprises condensing an azeotropic or azeotrope-like composition and thereafter evaporating said azeotropic or azeotrope-like composition in the vicinity of the body to be cooled, wherein said azeotropic or azeotrope-like composition consists essentially of Z-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzz.

Another embodiment of this invention provides a process using an azeotropic or azeotrope-like composition as a solvent, wherein said azeotropic or azeotrope-like composition consists essentially of and Z-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzzz.

Another embodiment of this invention provides a process for producing an aerosol product. The process comprises using an azeotropic or azeotrope-like composition as a propellant, wherein said azeotropic or azeotrope-like composition consists essentially of Z-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzz.

Another embodiment of this invention provides a process using an azeotropic or azeotrope-like composition as a heat transfer media, wherein said azeotropic or azeotrope-like composition consists essentially of and Z-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzzz.

Another embodiment of this invention provides a process for extinguishing or suppressing a fire. The process comprises using an azeotropic or azeotrope-like composition as a fire extinguishing or suppression agent, wherein said azeotropic or azeotrope-like composition consists essentially of Z-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzz.

Another embodiment of this invention provides a process using an azeotropic or azeotrope-like composition as dielectrics, wherein said azeotropic or azeotrope-like composition consists essentially of and Z-FC-1336mzz and a component selected from the group consisting of methyl formate, n-pentane, 2-methylbutane, 1,1,1,3,3-pentafluorobutane, trans-1,2-dichloroethylene, 1,1,1,3,3-pentafluoropropane, dimethoxymethane, cyclopentane and Z-FC-1336mzz.

The invention claimed is:

1. A composition consisting essentially of:
   (a) E-1,1,1,4,4,5,5,5-octafluoro-2-pentene; and
   (b) a component selected from the group consisting of methyl formate, n-pentane, 2-methylbutane, 1,1,1,3,3-pentafluoropropane, dimethoxymethane, cyclopentane and Z-1,1,1,4,4,4-hexafluoro-2-butene; wherein said component is present in an effective amount to form an azeotrope-like combination with the E-1,1,1,4,4,5,5,5-octafluoro-2-pentene.

2. A composition consisting essentially of:
   (a) E-1,1,1,4,4,5,5,5-octafluoro-2-pentene; and
   (b) a component selected from the group consisting of methyl formate, n-pentane, 2-methylbutane, cyclopentane and Z-1,1,1,4,4,4-hexafluoro-2-butene; wherein said component is present in an effective amount to form an azeotropic combination with the E-1,1,1,4,4,5,5,5-octafluoro-2-pentene.

3. A composition consisting essentially of:
   (a) E-1,1,1,4,4,5,5,5-octafluoro-2-pentene; and
   (b) a component selected from the group consisting of 2-methylbutane and Z-1,1,1,4,4,4-hexafluoro-2-butene; wherein said component is present in an effective amount to form an azeotrope-like combination with the E-1,1,1,4,4,5,5,5-octafluoro-2-pentene.

* * * * *